United States Patent
Koch et al.

(12) 
(10) Patent No.: US 6,551,626 B1
(45) Date of Patent: Apr. 22, 2003

(54) COMPOSITION CONTAINING PYRROLIZIDINE-ALKALOID-FREE PETASITES

(75) Inventors: Volkmar Koch, Utting/Ammersee (DE); Reiner Rittinghausen, Eching/Ammersee (DE)

(73) Assignee: Weber & Weber GmbH & Co. KG (DE)

(*) Notice: Subject to any disclaimer, the term of this patent is extended or adjusted under 35 U.S.C. 154(b) by 0 days.

(21) Appl. No.: 09/763,912

(22) PCT Filed: Jun. 29, 1999

(86) PCT No.: PCT/EP99/04484
§ 371 (c)(1),
(2), (4) Date: Feb. 23, 2001

(87) PCT Pub. No.: WO00/12107
PCT Pub. Date: Mar. 9, 2000

(30) Foreign Application Priority Data

Aug. 26, 1998 (DE) .......................................... 198 38 848

(51) Int. Cl.⁷ .............................................. A61K 35/78
(52) U.S. Cl. ...................... 424/725; 514/861; 514/863
(58) Field of Search .......................... 424/725; 514/861, 514/863

(56) References Cited

U.S. PATENT DOCUMENTS 5,384,121 A * 1/1995 Rhodes

FOREIGN PATENT DOCUMENTS

| AU | 9893357 | * | 5/1999 |
| DE | 3910831 | * | 12/1990 |
| DE | 4111141 | * | 10/1992 |
| DE | 4426267 | * | 2/1996 |
| DE | 19702168 | * | 10/1997 |
| EP | 74584 | * | 3/1983 |
| EP | 508330 | * | 10/1992 |
| EP | 0 391 594 B | | 10/1995 |
| FR | 8351 | * | 10/1967 |
| JP | 1283218 | * | 11/1989 |
| RO | 93835 | * | 2/1988 |
| RU | 2099986 | * | 12/1997 |
| SU | 1792707 | * | 2/1993 |

OTHER PUBLICATIONS

Bickel et al. Planta Med. 1994. vol. 60, pp. 318–322.*

Derwent Class B05, AN 1988–211090 (RO 93 835 A).

* cited by examiner

Primary Examiner—Christopher R. Tate
(74) Attorney, Agent, or Firm—Reed Smith LLP; Michael I. Wolfson

(57) ABSTRACT

The present invention relates to a pharmaceutical composition based on a petasites extract without a hepatoxic, carcinogenic, cytostatic and/or mutagenic effect, the use thereof and a method for the production thereof.

34 Claims, No Drawings

COMPOSITION CONTAINING PYRROLIZIDINE-ALKALOID-FREE PETASITES

BACKGROUND OF THE INVENTION

The present invention concerns a pharmaceutical composition based on petasites extract without hepatotoxic, carcinogenic, cytostatic and/or mutagenic effect, as well as its use and a method for its production.

Petasites extracts are isolated from the roots of the butterbur and have a spasmolytic and analgesic effect. This effect of butterbur was already known to Hippocrates, Galen and Paracelsus. The pharmaceutical preparations from petasites extract used now are viscous extracts from Rhizoma Petasites, i.e., extracts from the rootstock of the butterbur, which have an unpleasant, bitter taste, are not readily resorbable and thus have a slightly delayed pharmaceutical effect following administration.

The butterbur also contains eremophilane and pyrrolizidine alkaloids, in addition to other sesquiterpenes. The pyrrolizidine basic structure is common to the pyrrolizidine alkaloids. They are distributed worldwide in higher plants. Pyrrolizidine alkaloids and their N-oxides are found in the genus Petasites, among others. The pyrrolizidine alkaloids contained in the plant parts of the genus Petasites are characterized by significant hepatotoxic, carcinogenic and mutagenic, but also cytostatic properties. The toxicity of the pyrrolizidine alkaloids is connected with specific structural groups that have the following structural features:

double bonds in the 1,2-position of the pyrrolizidine ring,
  esterifications of at least the primary hydroxymethyl group with a $C_5$ or $C_6$ carboxylic acid,
  branching of the alkyl side chain with at least one of the necinic acids.

The cyclic diesters have the highest toxicity and carcinogenicity. The pyrrolizidine alkaloids are quickly resorbed after peroral intake, their N-oxides only after reduction by intestinal flora. On metabolism in the liver, the pyrrolizidine alkaloids are converted to very toxic pyrrole derivatives by oxidases with mixed functionality. These are very reactive and, under physiological conditions, alkylate the nucleophilic groups of DNA, like amino, thiol and hydroxy groups.

Pyrrolizidine alkaloid-containing medicinal plants have long been used in phytotherapy as natural drugs. Since the Federal Health Office (BGA) has classified all medicinal plants and their preparations containing toxic pyrrolizidine alkaloids as health hazards and potentially carcinogenic, intensive work was conducted to produce pharmaceutical petasites extracts that have a significantly reduced content of pyrrolizidine alkaloids.

Thus, methods are described in DE 39 10 831, DE 41 11 141, DE 41 41 749, with which the content of pyrrolizidine alkaloids in the extract can be reduced to less than 5 ppm, in the best case even below 0.1 ppm, but a truly pyrrolizidine alkaloid-free petasites extract cannot be obtained according to these methods.

The task of the present invention is to produce petasites extracts without hepatotoxic, carcinogenic, cytostatic and/or mutagenic effect.

Another task of the invention is to provide a method for production of petasites extracts without hepatotoxic, carcinogenic, cytostatic and/or mutagenic effect.

SUMMARY OF THE INVENTION

Another task of the invention is to produce petasites preparations without hepatotoxic, carcinogenic, cytostatic and/or mutagenic effect with a rapid and/or improved action.

The task of the present invention is solved by a pharmaceutical composition based on petasites extract in which the petasites extract is recovered from the plant and/or plant parts of the genus Petasites, the petasites extract is free of pyrrolizidine alkaloids, and in which magnesium and/or other pharmaceutically and/or physiologically active substances are optionally added to this pharmaceutical composition.

The task of the invention related to the process is solved by an extraction method in which the crude extract is subjected to subsequent final treatment in an aqueous medium with a pH value <7, preferably $\leq 4$.

DETAILED DESCRIPTION OF THE PREFERRED EMBODIMENTS

Petasites extract in the prior art has thus far been recovered from the rootstock of butterbur. It has now proven advantageous to recover the extract from plants and/or plant parts of *Petasites hybridus, Petasites albus, Petasites japonicus, Petasites paradoxus* and/or *Petasites spurius*, in which the underground plant parts are preferably used to produce the extract. Use of not only the underground plant parts to produce the extract, but also other plant parts has the advantage that a significantly higher yield of petasites extract is obtained, from to the entire plant.

In addition to the already known destraction methods with supercritical $CO_2$, as described, for example, in EP 0 392 504 and EP 0 547 465, petasites extracts according to the invention can also be produced with other destraction agents. Because of the temperature sensitivity of the natural extracts, solvents are chosen that can be converted to the supercritical state at temperatures below 100° C., preferably at $\leq 50°$ C., and have sufficient solvent capacity for lipophilic petasites active principles. Appropriate gases include ethylene (critical temperature 9.95° C.) and ethane (critical temperature 32.25° C.). Appropriate conditions for destraction of petasin from butterbur plant parts with ethylene and ethane lie at pressures of 1–50 MPa, preferably 8–30 MPa, and temperatures of 10–50° C. The crude petasites extracts recovered according to these methods contain up to 30% water, depending on the degree of preliminary drying of the initial material, which must then be separated. The crude extract can optionally be treated with a one- to ten-fold quantity of water, preferably with a pH value $\leq 7$, and then dried by usual methods.

It was found that, in the ordinary destraction process, especially during destraction of petasites with supercritical $CO_2$, the water content in the overall system plays a decisive role in separation of pyrrolizidine alkaloids. Deliberate enrichment of the extracted product with water before destraction leads to extracts with increased water contents of up to 50%, which exhibit better and more rapid phase separation and already yield extracts with significantly lower pyrrolizidine content right after separation of the aqueous phase. The extracted product for this purpose is brought to a total moisture content of 10–40 wt. %, preferably 15–30 wt. %, and especially 20–25 wt. %, before destraction by addition of water.

As an alternative, good alkaloid depletion can also be achieved by forcing water into the compressed solvent-extract mixture in the separator region of the extraction unit. For this purpose, about 10–50 wt. % water, from the amount of extract being separated, is forced into the separator device of the extraction unit before decompression of the solvent-extract mixture, and then decompressed. The extracts so obtained have pyrrolizidine alkaloid contents below 0.1 ppm after separation of the aqueous phase.

It has now also been surprisingly demonstrated that suitable crude extracts of petasites can also be obtained by extraction under subcritical conditions with gases liquefied under high pressure, instead of destraction with gases in the supercritical state.

Pressure-liquefied propane gas has proven to be particularly suitable for petasites extraction under subcritical conditions. Propane (critical temperature 97° C.) can be liquefied at room temperature under high pressure (critical pressure about 42 MPa). Ground petasites plant material is subjected to solid extraction with liquefied propane gas according to the usual methods in appropriate autoclave reactors. Here again, the deliberate enrichment of the extracted product with up to 40 wt. % water can be used to advantage for improved pyrrolizidine alkaloid separation, as well as subsequent forcing of water into the compressed propane-extract mixture.

The propane extraction method can be run in the temperature range from 15–40° C., preferably 20–30° C., and especially at room temperature. The employed extraction pressures lie in the range from 5 to 20 MPa, preferably 10 to 15 MPa, and especially at about 14 MPa, i.e., generally well below the typical destraction pressures. The crude extracts obtained after evaporation of the solvent contain a partially emulsified residual water content of up to 20% and surprisingly have a significantly depleted, very limited fraction of pyrrolizidine alkaloids relative to the initial material. Supernatant water can be separated by skimming or decanting. The limited quantities of water-soluble pyrrolizidine alkaloids in the crude extract can be completely separated by aqueous final treatment, preferably pH <7, and then phase separation, as described below. The extract can also be dried by means of ordinary desiccants, like sodium sulfate, magnesium sulfate, as well as molecular sieves, etc., and freed of emulsified water.

The advantage of this method according to the invention lies in the possible application of lower temperatures, for example, extraction at room temperature, and the lower pressures, which guarantee both cost-effective and mild extraction of the sensitive petasites extracts.

Another advantage, especially over to the ordinary supercritical $CO_2$ destraction method, consists of the more favorable solution properties of the liquid propane. Since propane, as a hydrocarbon, is able to dissolve the lipophilic petasins much better than the hydrophilic pyrrolizidine alkaloids, separation of both components is better and depletion of the undesired alkaloids from the petasites material is much more complete. The crude extracts recovered by subcritical propane extraction generally have a residual alkaloid content of well below 0.1 ppm. The attainable total yields of crude extract under comparable conditions are also higher overall.

The subcritical propane extraction according to the invention can be run in ordinary autoclave reactors batchwise or semicontinuously, and they can be designed as one- or multicomponent extraction units. Reactors with continuous extract separation with recycling of propane to the extraction autoclaves are to be preferred. for cost reasons and from an environmental standpoint. In addition, extraction can also be run in simple pressure reactors in one or more successive steps.

The water-containing extract can also be dried directly with an ordinary desiccant, preferably $Na_2SO_4$, without shaking the extract with water. For this purpose, the supernatant water is separated and the desiccant added to the extract in the required amount. The desiccant is then separated according to the usual method in the prior art, for example, by filtration or centrifuging.

To eliminate pyrrolizidine alkaloids with 0.01–10-fold, preferably 0.1–10-fold the amount of water of the extract, the extract can be treated in a continuous or batchwise extraction method.

The extract is optionally shaken at least once with 0.1- to 10-fold the amount of water with a pH value <7, preferably ≦4, especially pH ≦1, the acid phase separated, and the extract brought to a pH value of 3–7 by repeated washing. A mineral acid is preferably used as acid, especially sulfuric acid with a normality of 0.0001 to 1, preferably from 0.1 to 1.

The water content of the petasites extract can be reduced to well below 1 wt. % by means of a desiccant, preferably $Na_2SO_4$, and/or a centrifuge.

As an alternative, or in addition, the crude extracts can be taken up in an appropriate adsorption agent, like silica gel, alumina oxide, aluminosilicate, zeolite, zirconium oxide, titanium oxide and molecular sieves, and optionally extracted another time under destraction or extraction conditions with addition of water, preferably water vapor. It is then dewatered, as described above, or supernatant water is separated from the extract, for example, by careful decanting of the extract, in which the supernatant aqueous phase is then discarded. Water/extract phase separation can advantageously be produced by ultrasound. Accelerated formation of a sharp phase boundary is made possible by the action of ultrasound.

The extracts so obtained have a pyrrolizidine alkaloid content of ≦0.1 ppm when the content in the crude extract was up to 0.5 ppm. In another final treatment step, the extract is mixed at least twice, preferably 4 to 6 times, in a ratio of 1 part extract and 2 parts doubly distilled water at a water temperature of at least 40° C. The phases are then separated and, in the last step, emulsified residual water is bound by addition of ordinary desiccants, preferably sodium sulfate. The desiccant loaded with water is centrifuged.

To determine the pyrrolizidine alkaloid content in the trace range, an ELISA can be used, which is ordinarily more sensitive by a factor of 1,000 than the GC-MS coupling. Pyrrolizidine alkaloids could not be found in any case in the petasites extracts produced according to the invention.

The petasites extracts produced according to the method of the invention contain about 40% petasins (calculated as isopetasin) and can be used in pharmaceutical compositions without further processing.

An advantageous variant of the invention includes pharmaceutical compositions based on petasites extract with a content of magnesium, preferably with a content of >0–500 mg, especially 10–250 mg, and with particular preference 50–100 mg, referred to the overall composition.

It has been shown that the spasmolytic and analgesic effect of a pharmaceutical composition according to the invention based on petasites extract with a content of magnesium, is much more effective than with magnesium-free compositions. Thus, a significantly faster onset and longer lasting effect of the petasin-containing composition according to the invention with magnesium could be observed in the treatment of migraine in patients than with magnesium-free petasin-containing compositions.

The pharmaceutical effect of petasin-containing compositions could surprisingly also be increased by addition of at least one pharmaceutically and/or physiologically active substance, containing at least one antiphlogistic or analgesic, preferably extracts of *Chamomilla recutita, Rhizoma Curcumae longae, Rhizoma Curcumae xanthorrhizae, Curcumae xanthorrhiza, Cortex Salicis, Salicis purpurea, Salicis daphenoides* and/or *Tanacetum parthenium;* at least one trace element, preferably iron, cobalt, chromium, iodine, copper, manganese, zinc and/or selenium; at least one secretolytic or secretomotor agent, preferably extracts from licorice root, thyme and/or peppermint oil; at least one bronchospasmolytic, preferably extracts from ivy leaves; and/or vitamins, preferably vitamins A, B, C, D and/or E.

It was also found that resorption of the petasites-containing pharmaceutical composition according to the invention can be increased in the gastrointestinal tract if at least one emulsifier is added to this composition, like sodium alkylsulfate, alkyl sulfonate, alkyl carboxylate, alkyl alcoholate, preferably with an alkyl chain length of $C_{12}$–$C_{18}$; polyethylene glycol fatty alcohol ethers, at least one ester, as well as ethers of polyethylene glycol with higher fatty acids or fatty alcohols, and/or polyethylene glycol stearate, especially cetylstearyl alcohol and/or glycerol-polyethylene glycol ricinoleate, lecithin, soybean oil or polysorbate.

Another advantageous variant according to the invention includes a petasites-containing composition, in which resorption in the gastrointestinal tract is delayed.

This type of composition has the advantage that a larger amount of petasites extract per dose unit can be administered, which is then resorbed over an extended period. It is possible on this account to achieve a petasites active principle blood plasma level of the pharmaceutically active main active principle of the petasites extract over a period of at least 12–48 hours, preferably 24 hours, which permits two-fold, preferably single, administration of the pharmaceutical composition containing petasites per day.

Appropriate substances for this include the substances that are generally known to delay resorption in the gastrointestinal tract for liberation of lipophilic active principles. The substance that delays resorption is preferably chosen from the group of paraffins, preferably a solid paraffin at room temperature, with particular preference a hard paraffin.

A form of administration containing petasites extract according to the invention that can be administered orally can also be coated with a layer that is resistant to gastric juice and/or delays resorption.

A particular drawback of the petasites extract is its unpleasant, bitter taste. As a result, a form of administration that partially or fully liberates the active principle in the mouth/throat is not possible, since the taste of the petasites extract is perceived as unpleasant by patients and sometimes induces immediate nausea.

It has now been found that the bitter, extremely unpleasant taste of petasites or petasites extract can be effectively masked by addition of at least one taste-masking substance, in which the taste-masking substance is preferably an essential oil, essence, aromatic water, oil sugar, fruit flavoring, like strawberry, lemon, vanilla, etc., aromatic drug extracts, artificial flavorings, sugars, polyols with sweetening power, neutral-tasting thickeners, cyclodextrins and/or mixtures of these.

By addition of a taste-enhancing substance, teas, chewable tablets, juices, etc. containing the petasites extract can be administered.

The pharmaceutical composition containing the petasites extract according to the invention can be present in a liquid, solid or liposomal form of administration. It is advantageous according to the invention if the form of administration is a spray, an aerosol, a foam, an inhalate, a powder, a tablet, capsule, soft gelatin capsule, a chewable tablet, salve, cream, gel, suppository or an injection solution. It is particularly preferred if the pharmaceutical composition containing the petasites extract according to the invention is designed as a tablet, capsule or chewable tablet that contains the active principle in the form of microcapsules.

As possible additional plant substances for a petasites cream according to the invention, Calendula (tincture/extraction), Viola (tincture/extraction) and/or vitamins, preferably vitamin E, are particularly suitable.

It is advantageous according to the invention if the corresponding individual dose of the aforementioned forms of administration contains approximately 25 mg petasites extract, preferably <25 mg or >25 mg petasites extract, especially $\leq 15$ mg or $\geq 35$ mg petasites extract, in which the daily dose preferably lies in the range from 5–600 mg of petasites extract, especially in the range from 5–250 mg petasites extract.

The pharmaceutical composition containing the petasites extract according to the invention is particularly suited for the treatment of gastrointestinal diseases of all types, for example, endogenous and exogenous damage to the gastric and intestinal mucosa, gastrointestinal ulcerations and gastrites of all types, Crohn's disease and ulcerative colitis, as well as cough, asthma, pollinosis, eczemas, migraine, psoriasis, dysmenorrhea, high blood pressure, or for use as a spasmolytic and analgesic.

The pharmaceutical composition containing the petasites extract according to the invention is also suitable for production of a drug for long-term treatment or long-term therapy of patients, especially newborns, infants and small children.

The following examples further explain the invention without limiting it in any way:

EXAMPLE 1
Subcritical Propane Extraction of Petasites 500 g ground butterbur plant drug from Rhizoma Petasitidis with an average moisture content of 12.8 wt. %, a petasin content of about 0.8% and a content of pyrrolizidine alkaloids of about 20–30 ppm was extracted in an autoclave (25 L volume) at a temperature of 24° C. and a pressure of 13.8 MPa with about 6 kg propane in one step. The turbid crude extract (about 17 g) obtained after evaporation of the propane contains about 10% water and a pyrrolizidine alkaloid content of less than 0.1 ppm.

EXAMPLE 2
Aqueous Processing of the Crude Extract

The extract is shaken three times with a five-fold amount of 0.1 N sulfuric acid, the acid phase separated, the extract brought to a pH value of 3–7 by repeated washing with doubly distilled water, and the extract then brought back to a water content of 1 wt. %. The extract so obtained, according to GC-MS analysis, has no detectable pyrrolizidine alkaloids. This extract is then shaken 5 times in a ratio of 1 part extract to 2 parts doubly distilled water with a water temperature of at least 45° C. After each agitation, one waits for separation of the aqueous phase from the lipophilic extract phase by standing and supernatant water is then carefully poured off from the top. In the last step, 20 g of sodium sulfate is added after decanting. The sodium sulfate loaded with water is centrifuged.

An ELISA was then carried out to determine the residual pyrrolizidine alkaloid content in the petasites extract, in which no pyrrolizidine alkaloids could be detected any longer. The detection limit of an ELISA for pyrrolizidine alkaloids is more sensitive, than with GC-MS coupling, by at least a factor of 1,000.

EXAMPLE 3
Formula for a Slow-release Soft Gelatin Capsule

| Composition | Quality | Amount |
|---|---|---|
| Active principle | | |
| Extract Petasitidis e radice 30:1 | | 25.0 mg |
| Auxiliaries | | |
| Medium-chain triglycerides* | Ph. Eur. 1997 | 245.0 mg |
| Capsule shell | | |
| Glycerol 85% | Ph. Eur. 1997 | 23.52–27.60 mg |
| Dry substance from sorbitol solution 70% Noncrystalline | Ph. Eur. 1997 | 17.12–20.10 mg |
| Gelatine | Ph. Eur. 1997 | 80.89–94.96 mg |
| Iron oxide red | E 172 | 0.47–0.55 mg |
| Glycerol | Ph. Eur. 1997 | 1.60–1.88 mg |
| Iron oxide black | E172 | 1.13–1.33 mg |
| Coating | | |
| Eudragit RL (according to Fiedler) | | 1.0–15.0 mg |

*Additional lipids, in which the extract is soluble, include: olive oil, corn oil, soybean oil.

EXAMPLE 4
Formula for Gastric Juice-resistant Soft Gelatin Capsule

| Composition | Quality | Amount |
|---|---|---|
| Active principle | | |
| Extract Petasitidis e radice 30:1 | | 25.0 mg |
| Auxiliaries | | |
| Medium-chain triglycerides* | Ph. Eur. 1997 | 245.0 mg |
| Capsule shell | | |
| Glycerol 85% | Ph. Eur. 1997 | 23.52–27.60 mg |
| Dry substance from sorbitol solution 70% Noncrystalline gelatins | Ph. Eur. 1997 | 17.12–20.10 mg |
| Gelatine | Ph. Eur. 1997 | 80.89–94.96 mg |
| Iron oxide red | E 172 | 0.47–0.55 mg |
| Glycerol | Ph. Eur. 1997 | 1.60–1.88 mg |
| Iron oxide black | E 172 | 1.13–1.33 mg |
| Coating | | |
| Cellulose acetate phthalate | | 1.0–15.0 mg |

*Additional lipids, in which the extract is soluble, include: olive oil, corn oil, soybean oil.

Therapeutical plasma concentration 1 to 100 mg/L.

EXAMPLE 5
Injection Solution

The petasites extract is mixed 1:10 with highly purified soybean oil with addition of 0.1–2 wt. % egglecithin as emulsifier and the mixture emulsified to 0.5 to 2.0 wt. % in water for injection purposes.

Therapeutic plasma concentration 1 to 100 µg/L.

EXAMPLE 6
Liposomal Composition

The liposomes are produced from glycerophosphilipids, cholesterol and stearylamine and at least one lipid derivative, in which the butterbur extract is dissolved in the lipid phase of the liposomes.

Therapeutic plasma concentration 1 to 100 mg/l.

EXAMPLE 7
Extract Petasites e Rad. 30:1 in Liquid Form of Administration

| Composition 100 g contains: | Quality | Amount |
|---|---|---|
| Active principle | | |
| Extract Petasitidis e radice 30:1 | | 500 mg |
| Auxiliaries | | |
| Glycerol-polyethylene glycol ricinoleate | USP XXII | 4500 mg |
| Ethanol 43% | HAB 1 | 95,000 g |
| | | 100,000 g |

What is claimed is:

1. A method of treating at least one of pollinosis, dysmenorrhea, eczemas and psoriasis, comprising:
administering to a patient suffering from at least one of pollinosis, dysmenorrhea, eczemas and psoriasis a therapeutically effective amount of a petasites extract without hepatotoxic, carcinogenic, cytostatic and/or mutagenic effect derived from plants of the genus Petasites, whereby the petasites extract is free of detectable levels of pyrrolizidine alkaloids.

2. The method of claim 1, wherein the petasites extract is admixed with a pharmaceutically active substance selected from the group consisting of magnesium, at least one antiphlogistic, and at least one analgesic.

3. The method of claim 2, wherein the pharmaceutically active substance is magnesium.

4. The method of claim 1, wherein the plant source of the petasites extract is selected from the group consisting of Petasites hybrids, Petasites albus, Petasites japonicos, Petasites paradoxes, Petasites spurius and mixtures thereof.

5. The method claim of 4, wherein an underground part of the plant is utilized.

6. The method of claim 2, wherein the pharmaceutically and/or physiologically active substance is chosen from the group consisting of at least one antiphlogistic and analgesic.

7. The method of claim 2, wherein the antiphlogistic and/or analgesic is selected from the group consisting of an extract obtained from Chamomilla recutita, Rhizoma Curcumae longae, Rhizoma Curcumae xanthorrhizae, Curcumae xanthorrhizae, Cortex Salicis, Salicis purpurea, Salicis daphenoides and Tanacetum parthenium.

8. The method of claim 7, wherein petasites extract is further admixed with trace elements selected from the group consisting of iron, cobalt, chromium, iodine, copper, manganese, zinc and selenium.

9. The method of claim 2, wherein the petasites extract is further admixed with a secretolytic or secretomotor agent.

10. The method of claim 9, wherein the secretolytic or secretomotor agent is selected from the group consisting of extracts of licorice root, thyme andlor peppermint oil.

11. The method of claim 6, wherein the petasites extract is further admixed with bronchospasmolytic.

12. The method of claim 11, wherein the bronchospasmolytic is selected from the group consisting of extracts from ivy leaves, Calendula, Viola and vitamins.

13. The method of claim 1, wherein the petasites extract is admixed further with at least one of vitamins A, B, C, D and E.

14. The method of claim 1, wherein the petasites extract is admixed further with at least one substance that increases resorption in the gastrointestinal tract.

15. The method of claim 14, wherein the substance that increases resorption includes an emulsifier.

16. The method of claim 15, wherein the emulsifier is selected from the group consisting of sodium alkyl sulfate, alkyl sulfonate, alkyl carboxylate, alkyl alcoholate having an alkyl chain length from $C_{12}$–$C_{18}$, polyethylene glycol fatty alcohol ether; esters of polyethylene glycol with higher fatty acids or fatty alcohols and/or polyethylene glycol stearate; cetylstearyl alcohol and glycerol polyethylene glycol ricinoleate.

17. The method of claim 1, wherein the petasites extract is admixed further with at least one substance that delays resorption in the gastrointestinal tract.

18. The method of claim 17, wherein the substance that delays resorption is a paraffin.

19. The method of claim 18, wherein the paraffin is a hard paraffin solid at room temperature.

20. The method of claim 1, wherein the petasites extract is further admixed with a taste-making substance.

21. The method of claim 20 wherein the taste-making substance is at least one member selected from the group consisting of essential oils, essences, aromatic waters, oil sugars, fruit flavorings, aromatic drug extracts, artificial flavorings, sugars, polyols with sweetening power, neutral-tasting thickeners, cyclodextrins and mixtures thereof.

22. The method of claim 1 wherein the petasites extract is administered orally and the pharmaceutical composition includes a layer resistant to gastric juices.

23. The method of claim 22, wherein the layer resistant to gastric juices is cellulose acetate phthalate.

24. The method of claim 1, wherein the petasites extract is prepared by extraction of petasites plant parts with one of compressed ethylene and ethane under supercritical conditions at temperatures below 100° C. and at a pressure of 1–50 Mpa to form a crude extract, and the crude extract, after separation of the solvent, is treated with a one- to ten-fold amount of water, and then dried.

25. The method of claim 1, wherein the Petasites extract is prepared by extraction of petasites plant parts with pressure-liquified propane under subcritical conditions in the temperature range from 15–40° C. and extraction pressures from 5–20 Mpa.

26. The method of claim 1, wherein the petasites extract is in liquid, semisolid, solid or liposomal form.

27. The method of claim 1, wherein the petasites extract is in the form of a spray, an aerosol, a foam, an inhalate, a powder, a tablet, a capsule, a soft gelatin capsule, a chewable tablet, a salve, a cream, a gel, a suppository or an injection solution.

28. The method of claim 1, wherein the petasites extract is in the form of a tablet, capsule or chewable tablet formed from microcapsules.

29. The method of claim 1, wherein the petasites extract is an orally administerable solid including a layer resistant to gastric juices.

30. The method of claim 29, wherein the layer resistant to gastric juices is cellulose acetate phthalate.

31. The method of claim 1, wherein the petasites extract is administered in a dosage containing between about 5 to 600 mg petasites extract.

32. The method of claim 1, wherein the petasites extract is administered in a dosage containing between about 15 to 30 mg petasites extract.

33. The method of claim 1, wherein the petasites extract is administered in a dosage of about 25 mg petasites extract.

34. The method of claim 1, wherein the petasites extract is prepared by extraction of petasite plant parts with compressed carbon dioxide under super critical conditions and water is added to at least one of the compressed carbon dioxide and the compressed carbon dioxide-extract mixture.

* * * * *